United States Patent [19]

Kohler et al.

[11] Patent Number: 6,121,480
[45] Date of Patent: Sep. 19, 2000

[54] METHOD FOR PRODUCING UNSYMMETRICALLY SUBSTITUTED BIPHENYLS

[75] Inventors: Bernd Kohler, Constance; Manfred Langer, Bingen; Thomas Mosandl, Radolfzell, all of Germany

[73] Assignee: Great Lakes Chemical Konstanz GmbH, Constance, Germany

[21] Appl. No.: 09/117,958

[22] PCT Filed: Feb. 24, 1997

[86] PCT No.: PCT/IB97/00266

§ 371 Date: Sep. 29, 1998

§ 102(e) Date: Sep. 29, 1998

[87] PCT Pub. No.: WO97/30970

PCT Pub. Date: Aug. 28, 1997

[30] Foreign Application Priority Data

Feb. 26, 1996 [DE] Germany .................. 196 07 135

[51] Int. Cl.[7] .................................................. C07C 255/00
[52] U.S. Cl. ........................................... 558/411; 558/423
[58] Field of Search ..................... 558/411, 423

[56] References Cited

U.S. PATENT DOCUMENTS 4,956,507  9/1990  Matson et al. ..................... 570/140
5,288,895  2/1994  Bouisset et al. ..................... 558/378

FOREIGN PATENT DOCUMENTS 0 566 468  10/1993  European Pat. Off. .
39 30 663  11/1990  Germany .

OTHER PUBLICATIONS

Minato, A., et al, "Selective Mono–alkylation and Arylation of Dihalides by Palladium–Catalyzed Cross–Coupling with the Gringnard and Organozinc Reagents", (21), 847, 1980.

Chemical Abstracts, vol. 125, No. 9, Aug. 26, 1996 p. 1136 col. 2 and N.A. Bumagin et al., *ZH. Org. Khim.,* vol. 31, No. 11 1995 pp. 1650–1656.

*Primary Examiner*—Joseph K. McKane
*Assistant Examiner*—Joseph Murray
*Attorney, Agent, or Firm*—Seidel, Gonda, Lavorgna & Monaco, PC

[57] ABSTRACT

The invention concerns a method for the production of unsymmetrically substituted cyanobiphenyls by the slow addition of an aryl Grignard compound to an optionally substituted bromobenzonitrile in the presence of a palladium complex catalyst.

15 Claims, No Drawings

METHOD FOR PRODUCING UNSYMMETRICALLY SUBSTITUTED BIPHENYLS

This application is a 371 of PCT/IB97/00266 filed on Feb. 24, 1997.

This invention concerns a method for producing unsymmetrically substituted biphenylcarbonitriles.

Some angiotensin II inhibitors contain a biphenyl residue as part of the molecule. The synthesis of these pharmaceutically active substances requires the use of unsymmetrically substituted biphenyls as starting materials or intermediates from which the final synthesis of the target molecule can be carried out. There is therefore a requirement for a simple and reliable method for the synthesis of unsymmetrically substituted biphenyls, which can be meaningfully incorporated into an economical overall process. This requires in particular a high selectivity and high yield. A special significance in this connection attaches to biphenyl derivatives bearing a cyano function.

Unsymmetrically substituted biphenyl- and biaryl-compounds are also suitable for use as liquid crystal compounds and as a part of electro-optical components, in particular for use in non-linear optics.

Methods which have been suggested for the synthesis of unsymmetrically substituted cyanobiphenyls include the reaction of organo-boron, zinc or tin compounds with bromobenzonitriles [J.Organometallic Chem. 390(1990) 389–3981]. The palladium-catalysed coupling of an aryl Grignard compound with an iodo-substituted benzonitrile has also been described. A method for the synthesis of 4'-methylbiphenyl-2-carbonitrile has been disclosed [EP 566468 A] in which a halobenzonitrile is treated with 4-methylphenyl-magnesium halide in the presence of a manganese salt as catalyst. These methods suggest that the very low yields observed under palladium catalysis are open to considerable improvement. For example, the authors of EP 566468 A saw a yield of only 1% on the reaction of 2.2 equivalents of 4-methylphenylmagnesium bromide with 2-bromobenzonitrile in the presence of catalytic amounts of tetrakis (triphenylphosphine)-palladium over 6 hours at 65° C. In this investigation the reactants were mixed together all at once.

On theoretical grounds, it would be expected that the coupling of an aryl Grignard compound with a haloaryl compound with electron-withdrawing functionality would produce the desired biaryl coupling-product in high selectivity and with high yield [see J.Organometallic Chem. 390(1990)389–398, especially Table 1 on page 391]. In the present state of the art, this requires that on addition of the Grignard reagent the carbon-halogen bond of the aryl halide with which the Grignard reagent reacts is considerably more reactive than any other electron-accepting groups which may be present in the substrate molecule. These considerations in practice exclude the use of bromobenzonitrile as a coupling partner, if high selectivity and high yield are to be achieved.

The present invention comprises a simple to carry out method for the synthesis of unsymmetrically substituted cyanobiphenyl and cyanobiaryl compounds in high selectivity and with high yield. A further object of the invention is to make possible a general method for obtaining compounds incorporating a biphenyl or biaryl structure. In particular, a highly selective, simple and economical synthesis of the unsymmetrically substituted cyanobiphenyl compounds would make possible a simple synthesis of such target molecules as angiotensin II inhibitors.

We have now found that by slow addition (i.e. addition over a relatively long time scale) of a solution of an aryl Grignard compound to a reaction medium containing a bromobenzonitrile and a suitable palladium complex catalyst coupling takes place with as the main reaction the formation of biphenylcarbonitrile. The main reaction resulting when the reactants are mixed all at once, i.e. the addition of the Grignard compound to the nitrile function, is by this means almost entirely suppressed. The formation of imines (and after hydrolysis, benzophenones) is not observed to any significant extent.

The high selectivity arising from this method, which leads almost exclusively to the desired biphenylcarbonitrile, is surprising on the basis of current knowledge. Further advantages of the method of the invention include simplicity, avoidance of loss of material, and a high yield.

According to the invention there is provided a method for the synthesis of unsymmetrically substituted biphenyls of the general formula

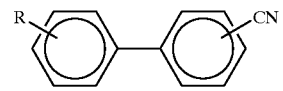

where R=H, alkyl, alkoxy, F, Cl or 4-phenylmethoxy by the palladium-catalysed coupling of an aryl Grignard compound of the general formula

where R=H, alkyl, alkoxy, F, Cl or 4-phenylmethoxy; X=Cl, Br or I, in which the ring bearing substituent R may also have further substituents, with bromobenzonitrile (which may bear further substituents), at 10–100° C., characterized in that the Grignard compound is added slowly over a period of at least 30 minutes and the palladium catalyst is added at a concentration of 0.1 to 20.0% molar based on the bromobenzonitrile.

Slow addition in the manner of the invention has the effect that the reactants are not immediately brought into contact with one another by mixing, but that the addition of the Grignard compound to the bromobenzonitrile is controlled and takes place over a longer time-scale. In contrast, the effect of immediate addition is that the reactants are mixed together over a time-scale of (for example) less than ten minutes. As our investigations have shown, such a method does not lead to the production of the desired unsymmetrically substituted biphenylcarbonitrile in either high yield or high selectivity. Slow addition means that (for example) the Grignard compound is added to 0.5 to 2 equivalents of the bromobenzonitrile over at least 30 minutes. Simple experiments may be required here to optimise the addition time. The addition time for the Grignard compound may be 1–24 hours. It is usually in the range 4–18, preferably 8–10, hours. In any case, the addition rate is so adjusted that concurrent formation of imines and benzophenones is minimised. This time scale also depends on the amount and nature of the catalyst added. A range of palladium catalysts is suitable for the purpose. As a rule the concentration of the catalyst should be 0.1 to 20.0% molar (based on the bromobenzonitrile), preferably 1.0 to 2.0% molar.

The aryl Grignard compounds used in the invention have the general formula

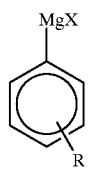

where R=H, alkyl, alkoxy, F, Cl or 4-phenylmethoxy; X=Cl, Br or I. The aromatic ring may bear further substituents, so long as they do not interfere with the reactivity of the Grignard function. In particular, acetal and alkyl groups do not interfere with the reaction. "Alkyl" here in principle includes any type of substituted or unsubstituted 1–30C alkyl group or 3–20C cycloalkyl group. Our investigations have shown that straight or branched chain alkyl groups can be used with an upper limit somewhere between 25 and 30 carbon atoms. The bromobenzonitrile can also bear other substituents corresponding to the above definitions, with obvious limitations imposed by undesirable reactivity or steric hindrance.

The yield of the desired unsymmetrically substituted biphenyls is usually higher by the method of the invention than by methods of the prior art. Reactions carried out as described, in contrast to most of the previously described synthetic routes, require no auxiliary base. This results in less effluent and a simpler process.

The essential point of the invention is the addition time of the aryl Grignard compound solution to the reaction medium containing the other components, which has crucial significance for the course of the reaction. As shown in Table 1 below the reaction of 4-methoxyphenylmagnesium bromide with 4-bromobenzonitrile catalysed by 2% (molar) palladium acetate/triphenylphosphine, with immediate the reaction of 4-methoxyphenylmagnesium bromide with 4-bromobenzonitrile catalysed by 2% (molar) palladium acetate/triphenylphosphine, with immediate mixing of the reactants, produces a mixture of 4'-methoxybiphenyl-4-carbonitrile and 4-bromo-4'-methoxybenzophenoneimine in the ratio 1:3 [see Comparative Example 2]. As expected, the main reaction is addition of the Grignard compound to the nitrile function. Longer addition times skew the product spectrum more and more in the direction of the biphenyl compound, until at an addition time of several hours the biphenylcarbonitrile is formed with high selectivity.

TABLE 1

Product ratio against Grignard compound addition time[a]

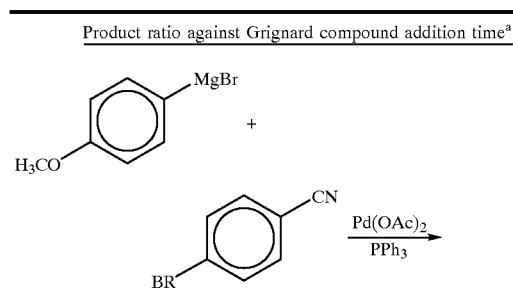

TABLE 1-continued

| Addition time (hours) | Ratio (A:B)[b] |
|---|---|
| 0 | 1:3 |
| 2 | 2:1 |
| 6 | 5:1 |
| 9 | 20:1 |

Notes:
[a] T = 20–25° C.; tetrahydrofuran; 2% (molar) Pd(OAc)$_2$/2PPh$_3$; 1.1 equivalents of Grignard compound.
[b] A:B yield ratio determined by HPLC. Total yield (A + B) exceeds 90%.

Suitable catalysts include all Pd(0) complexes such as Pd(PPh$_3$)$_4$ which are known to be catalytically active in reactions of the type which this invention concerns (often called Suzuki or Heck coupling). The catalytically active Pd(0) species can be generated in situ from Pd(II) compounds. In a preferred way of carrying out the reaction, the catalytically active species is produced in situ by the addition of a mixture of PdCl$_2$ and triphenylphosphine (in the molar ratio 1:2) under the influence of the Grignard compound. The amount of catalyst added depends on the requirements of the particular system. As a rule the palladium compound is added at a molar concentration of 0.1% to 20% relative to the benzonitrile. Larger amounts of catalyst do not adversely affect the course of the reaction, but are undesirable on economic grounds. As an example Table 2 illustrates the use of various amounts of catalyst in the coupling of 4-(phenylmethoxy)phenylmagnesium bromide with 4-bromobenzonitrile.

TABLE 2

Product ratio against amount of catalyst[a]

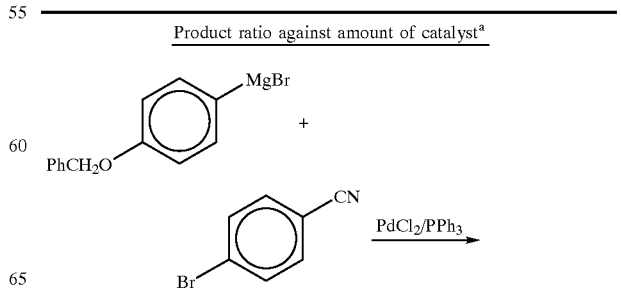

TABLE 2-continued

| | |
|---|---|
| 4 | >100:1 |
| 2 | >100:1 |
| 0.4 | >100:1 |

Notes:
[a] T = 67–69° C.; tetrahydrofuran; addition time of Grignard compound (1.1 equivalents) 8–9 hours.
[b] molar % relative to 4-bromobenzonitrile.
[c] yield ratio of C and D determined by HPLC; total yield (C + D) is greater than 95%.

Any organic solvent inert towards the Grignard compound is a suitable reaction medium, for example tetrahydrofuran, 2-methyltetrahydrofuran, acyclic ethers or acetals. Tetrahydrofuran and 2-methyltetrahydrofuran are preferred.

The reaction temperature is in the range 10–100° C. The reaction temperature preferably lies in the range of 20–80° C.

The molar ratio of bromobenzonitrile to Grignard compound is preferably 2:1 to 1:2 and especially between 1:1 and 1:1.2 at which higher yields and better quality product may be obtained.

The method here described permits the synthesis of unsymmetrically substituted biphenylcarbonitriles with substituents at any position (ortho, meta or para). All functional groups on the bromobenzonitrile which are compatible with the Grignard function are allowable as substituents. The examples below use alkyl, halogen and alkoxy substituents.

The invention is further illustrated by means of the following Examples.

EXAMPLE 1

4-methoxyphenylmagnesium bromide (112 g, 16% solution in tetrahydrofuran) is added dropwise over nine hours at 20–25° C. to a solution of 4-bromobenzonitrile (14 g), palladium (II) acetate (0.35 g), and triphenylphosphine (0.81 g) in tetrahydrofuran (100 ml). [HPLC: total yield >90%; 4'-methoxybiphenyl-4-carbonitrile to 4-bromo-4'-methoxybenzophenoneimine ratio 20:1]. Water (20 ml) is added and tetrahydrofuran removed under vacuum. The residue is extracted with toluene (110 ml). Insoluble material is filtered off and the filtrate evaporated down. The crude product is recrystallised from ethanol to give 4'-methoxybiphenyl-4-carbonitrile (12 g, 75%) as a solid, m.pt 102–104° C. $^1$H NMR (CDCL$_3$):3.85 (s,3H), 6.99 (d,2H), 7.52 (d,2H), 7.62 (d,2H), 7.68 (d,2H).

EXAMPLE 2

4-methoxyphenylmagnesium bromide (91 g, 14% solution in tetrahydrofuran) is added dropwise over 6 hours at 20–25° C. to a solution of 4-bromobenzonitrile (10 g), palladium (II) acetate (0.25 g) and triphenylphosphine (0.58 g) in tetrahydrofuran (80 ml). [HPLC: total yield >90%; ratio 4'-methoxybiphenyl-4-carbonitrile to 4-bromo-4'-methoxybenzophenoneimine 5:1].

EXAMPLE 3

4-methoxyphenylmagnesium bromide (91 g, 14% solution in tetrahydrofuran) is added dropwise at 20–25° C. over two hours to a solution of 4-bromobenzonitrile (10 g), palladium (II) acetate (0.25 g) and triphenylphosphine (0.58 g) in tetrahydrofuran (80 ml). [HPLC: total yield >90%; ratio 4'-methoxybiphenyl-4-carbonitrile to 4-bromo-4'-methoxybenzophenoneimine 2:1].

EXAMPLE 4

4-(phenylmethoxy)phenylmagnesium bromide 759 g, 25% solution in tetrahydrofuran) is added dropwise over nine hours at 20–25° C. to a solution of 4-bromobenzonitrile (109 g), palladium (II) chloride (4.2 g) and triphenylphosphine (13 g) in tetrahydrofuran (420 ml). After cooling to room temperature and addition of water (340 ml), the tetrahydrofuran is distilled off under vacuum. Toluene (680 ml) is added and the aqueous phase separated at 85° C. The organic phase is filtered hot (80–85° C.). [HPLC: total yield >90%; ratio 4'-(phenylmethoxy)biphenyl-4-carbonitrile to 4-bromo-4'-(phenylmethoxy)benzophenone 10:1]. Toluene (340 ml) is distilled off. On cooling to room temperature, 4'-(phenylmethoxy)biphenyl-4-carbonitrile (110 g, 64%) crystallises out, m.pt. 146–148° C. $^1$H NMR (CDCl$_3$): 5.10(s,2H), 7.06 (d,2H), 7.32–7.47 (m,5H), 7.52 (d,2H), 7.62 (d,2H), 7.68 (d,2H).

EXAMPLE 5

4-(phenylmethoxy)phenylmagnesium bromide (809 g, 27% solution in tetrahydrofuran) is added dropwise over eight hours to a refluxing solution of 4-bromobenzonitrile (128 g), palladium (II) chloride (0.50 g) and triphenylphosphine (1.5 g) in tetrahydrofuran (500 ml). After cooling to room temperature and addition of water (400 ml), tetrahydrofuran is removed under vacuum. Toluene (800 ml) is added and the aqueous phase removed at 85° C. The organic phase is filtered hot. [HPLC: total yield >95%; ratio 4'-(phenylmethoxy)biphenyl-4-carbonitrile to 4-bromo-4'-(phenylmethoxy)benzophenone >100:1]. Toluene (400 ml) is distilled off. On cooling to room temperature, 4'-(phenylmethoxy)biphenyl-4-carbonitrile (178 g, 89%) crystallises out.

EXAMPLE 6

4-(phenylmethoxy)phenylmagnesium bromide (108 g, 21% solution in tetrahydrofuran) is added dropwise over eight hours to a refluxing solution of 4-bromobenzonitrile (13 g), palladium (II) chloride (51 mg) and triphenylphosphine (150 mg) in tetrahydrofuran (50 ml). After cooling to room temperature and addition of water (40 ml), tetrahydrofuran is removed under vacuum. Ethanol (30 ml) and 25% hydrochloric acid (2 ml) are added and the mixture refluxed for two hours. [HPLC: total yield >95%; ratio 4'-(phenylmethoxy)biphenyl-4-carbonitrile to 4-bromo-4' (phenylmethoxy)benzophenone >100:1).

EXAMPLE 7

4-(phenylmethoxy)phenylmagnesium bromide (108 g, 21% solution in tetrahydrofuran) is added dropwise over nine hours to a refluxing solution of 4-bromobenzonitrile (13 g), palladium (II) chloride (0.25 g) and triphenylphosphine (0.75 g) in tetrahydrofuran (50 ml). After cooling to room temperature and addition of water (40 ml), tetrahydrofuran is removed under vacuum. Ethanol (30 ml) and 25% hydrochloric acid (2 ml) are added and the mixture refluxed for two hours. [HPLC: total yield >95%; ratio 4'-(phenylmethoxy)biphenyl-4-carbonitrile to 4-bromo-4'-(phenylmethoxy)benzophenone >100:11].

EXAMPLE 8

4-(phenylmethoxy)phenylmagnesium bromide (108 g, 21% solution in tetrahydrofuran) is added dropwise over nine hours to a refluxing solution of 4-bromobenzonitrile (13 g), palladium (II) chloride (0.51 g) and triphenylphosphine (1.5 g) in tetrahydrofuran (50 ml). After cooling to room temperature and addition of water (40 ml), tetrahydrofuran is removed under vacuum. Ethanol (30 ml) and 25% hydrochloric acid (2 ml) are added and the mixture refluxed for two hours. [HPLC: total yield >95%; ratio 4'(phenylmethoxy)biphenyl-4-carbonitrile to 4-bromo-4'-(phenylmethoxy)benzophenone >100:1].

EXAMPLE 9

4-methylphenylmagnesium chloride (610 g, 21% solution in tetrahydrofuran) is added dropwise over eight hours to a refluxing solution of 2-bromobenzonitrile (140 g), palladium (II) chloride (1.4 g) and triphenylphosphine (4.0 g) in tetrahydrofuran (375 ml). [HPLC: 4'methylbiphenyl-2-carbonitrile >95%, 2-bromo-4'-methylbenzophenoneimine >0.2%]. After cooling to room temperature tetrahydrofuran is removed under vacuum. Water (100 ml) and toluene (360 ml) are added. After separation of the aqueous phase, the crude product is distilled at 110–112° C./0.1 mbar, to give 4'-methylbiphenyl-2-carbonitrile (131 g, 88%) as a solid, m.pt. 50–52° C. $^1$H NMR (CDCL$_3$): 2.40(s,3H), 7.30(d,2H), 7.37–7.52(m,4H), 7.59–7.66 (m.1H), 7.75(m,1H).

EXAMPLE 10

4-methylphenylmagnesium chloride (100 g, 20% solution in tetrahydrofuran) is added dropwise over two hours to a refluxing solution of 2-bromobenzonitrile (22 g), palladium (II) chloride (0.21 g) and triphenylphosphine (0.63 g) in tetrahydrofuran (60 ml). After cooling to room temperature and addition of water (40 ml), tetrahydrofuran is removed under vacuum. Ethanol (30 ml) and 25% hydrochloric acid (2 ml) are added and the mixture refluxed for two hours. [HPLC: total yield >90%; ratio 4'-methylbiphenyl-2-carbonitrile to 2-bromo-4'-methylbenzophenone 5.1].

EXAMPLE 11

4-methylphenylmagnesium chloride (111 g, 18% solution in 2-methyltetrahydrofuran) is added dropwise over eight hours to a refluxing solution of 2-bromobenzonitrile (22 g), palladium (II) chloride (0.21 g) and triphenylphosphine (0.63 g) in 2-methyltetrahydrofuran (60 ml). After cooling to room temperature and addition of water (40 ml), 2-methyltetrahydrofuran is removed under vacuum. Ethanol (30 ml) and 25% hydrochloric acid (2 ml) are added and the mixture refluxed for two hours. [HPLC: total yield >95%; ratio 4'-methylbiphenyl-2-carbonitrile to 2-bromo-4'-methylbenzophenone 10:1].

EXAMPLE 12

4-methylphenylmagnesium chloride (10 g, 20% solution in diethoxymethane) is added dropwise over nine hours to a refluxing solution of 2-bromobenzonitrile (22 g), palladium (II) chloride (0.21 g) and triphenylphosphine (0.63 g) in diethoxymethane (60 ml). After cooling to room temperature and addition of water (40 ml), diethoxymethane is removed under vacuum. Ethanol (30 ml) and 25 % hydrochloric acid (2 ml) are added and the mixture refluxed for two hours. [HPLC: total yield >95%; ratio 4'-methylbiphenyl-2-carbonitrile to 2-bromo-4'-methylbenzophenone about 100:1].

EXAMPLE 13

4-methylphenylmagnesium chloride (49 g, 20% solution in tetrahydrofuran) is added dropwise over eight hours to a refluxing solution of 3-bromobenzonitrile (10 g), palladium (II) acetate (2.4 g) and triphenylphosphine (5.8 g) in tetrahydrofuran (200 ml). [HPLC: yield 89–91%]. After cooling to room temperature tetrahydrofuran is removed under vacuum. The residue is taken up in toluene/water (3:1) (200 ml ) and the aqueous phase separated off. The solvent is removed by distillation and the crude product purified by column chromatrography (Kieselgel 60; n-hezane/acetone 3:1) to give 4'-methylbiphenyl-3-carbonitrile as a solid, m.pt. 59–61° C. $^1$H NMR (CDCl$_3$): 2.41(s,3H), 7.29(d,2H), 7.46(d,2H), 7.49–7.63(m,2H) 7.77–7.85(m,2H).

EXAMPLE 14

4-methylphenylmagnesium chloride (98 g, 20% solution in tetrahydrofuran) is added dropwise over five hours to a refluxing solution of 4-bromobenzonitrile (20 g), palladium (II) chloride (0.78 g) and triphenylphosphine (2.3 g) in tetrahydrofuran (100 ml). [HPLC: yield 91–93%]. After cooling to room temperature tetrahydrofuran is removed under vacuum. The residue is taken up in toluene/water (1:1) (200 ml) and filtered. The aqueous phase is separated off. Solvent is removed by distillation and the crude product recrystallised from ethanol to give 4'-methylbiphenyl-4-carbonitrile as a solid, m.pt. 107–109° C. $^1$H NMR (CDCl$_3$): 2.41(s,3H), 7.29(d,2H), 7.49(d,2H), 7.66 (d,2H), 7.71 (d,2H).

EXAMPLE 15

2-methylphenylmagnesium bromide (82 g, 31% solution in tetrahydrofuran) is added dropwise over eleven hours to a refluxing solution of 4-bromobenzonitrile (20 g), palladium (II) chloride (0.78 g) and triphenylphosphine (2.3 g) in tetrahydrofuran (100 ml). [HPLC: yield 92–94%]. After cooling to room temperature, tetrahydrofuran is removed under vacuum. The residue is taken up in toluene/water (3:1) (300 ml) and the aqueous phase separated off. The solvent is removed by distillation and the crude product purified by column chromatography on Kieselgel 60 using n-hexane/acetone (3:1). This gives 2'-methylbiphenyl-4-carbonitrile as an oil. $^1$H NMR (CDCl$_3$): 2.25(s,3H), 7.10–7.32(m,4H), 7.43(d,2H), 7.71(d,2H).

EXAMPLE 16

3-methoxyphenylmagnesium bromide (95 g, 29% solution in tetrahydrofuran) is added dropwise over nine hours to a refluxing solution of 4-bromobenzonitrile (20 g), palladium (II) chloride (0.78 g) and triphenylphosphine (2.3 g) in tetrahydrofuran (200 ml). [HPLC: yield 90–92%]. After cooling to room temperature the tetrahydrofuran is removed under vacuum. The residue is taken up in toluene/water (3:1) (300 ml) and the aqueous phase separated off. The solvent is removed by distillation and the crude product purified by column chromatography on Kieselgel 60 using n-hexane/acetone (3:1). This gives 3'-methoxybiphenyl-4-carbonitrile as an oil. $^1$H NMR (CDCl$_3$): 3.87(s,3H), 6.94–6.98(m,1H), 7.10(t,1H), 7.14–7.19(m,1H), 7.40(t,1H), 7.67(d,2H), 7.72 (d,2H).

EXAMPLE 17

4-methoxyphenylmagnesium bromide (280 g, 15% solution in tetrahydrofuran) is added dropwise over seven hours to a refluxing solution of 2-bromobenzonitrile (32 g), palladium (II) chloride (1.3 g) and triphenylphosphine (3.8 g) in tetrahydrofuran (210 ml). [HPLC: yield 94–95%]. After cooling to room temperature and the addition of water (50 ml), tetrahydrofuran is removed under vacuum. The residue is extracted with toluene (230 ml). Insoluble material is filtered off and the solvent distilled off. The crude product is recrystallised from ethanol to give 4'-methoxybiphenyl-2-carbonitrile as a solid, m.pt. 82–83° C. $^1$H NMR (CDCl$_3$): 3.90(s,3H), 7.02(d,2H), 7.36–7.52(m,4H), 7.59–7.65(m, 1H), 7.74(d,1H).

EXAMPLE 18

4-octyloxyphenylmagnesium bromide (124 g, 25% solution in tetrahydrofuran) is added dropwise over ten hours to a refluxing solution of 4-bromobenzonitrile (17 g), palladium (II) chloride (0.68 g) and triphenylphosphine (2.0 g) in tetrahydrofuran (100 ml). [HPLC: yield 92–94%]. After cooling to room temperature tetrahydrofuran is removed under vacuum. Water (20 ml) and toluene (150 ml) are added and the mixture filtered hot (80–85 C.). The aqueous phase is separated off, and the solvent removed by distillation. The crude product is recrystallised from ethanol/n-hexane to give 4'-octyloxybiphenyl-4-carbonitrile as a solid. $^1$H NMR (CDCl$_3$): 0.89(t,3H), 1.29–1.50(m,10H), 1.81(quint.2H), 4.00(t,2H), 6.99(d,2H), 7.52(d,2H), 7.63(d,2H), 7.68(d,2H).

EXAMPLE 19

4-chlorophenylmagnesium chloride (114 g, 18% solution in tetrahydrofuran) is added dropwise over seven hours to a refluxing solution of 4-bromobenzonitrile (20 g), palladium (II) chloride (0.78 g) and triphenylphosphine (2.3 g) in tetrahydrofuran (100 ml). [HPLC: yield 75–79%]. After cooling to room temperature tetrahydrofuran is removed under vacuum. The residue is taken up in toluene/water (1:1) (200 ml) and filtered. The aqueous phase is separated off, and the solvent removed by distillation. The crude product is recrystallised from isopropanol/ethanol to give 4'-chlorobiphenyl-4-carbonitrile as a solid, m.pt. 128–130° C. $^1$H NMR (CDCl$_3$): 2.41(s,3H), 7.46(d,2H), 7.53(d,2H), 7.65(d,2H), 7.74(d,2H).

EXAMPLE 20

2,5-dimethylphenylmagnesium bromide (84 g, 20% solution in tetrahydrofuran) is added dropwise over five hours to a refluxing solution of 4-bromo-2-methylbenzonitrile (16 g), palladium (II) chloride (0.57 g) and triphenylphosphine (1.7 g) in tetrahydrofuran (100 ml). [HPLC: yield 90–95%]. After cooling to room temperature tetrahydrofuran is removed under vacuum. The residue is taken up in toluene/water (1:1) (200 ml) and filtered. The aqueous phase is separated off, and the solvent removed by distillation. The crude product is recrystallised from ethanol to give 3,2',5'-trimethylbiphenyl-4-carbonitrile as a solid, m.pt. 96–97° C. $^1$H NMR (CDCl$_3$): 2.19(s,3H), 2.34(s,3H), 2.58(s,3H), 6.99 (s,1H), 7.08–7.25(m,3H), 7.62(d,1H).

Comparative Example 1

4-methoxyphenylmagnesium bromide (78 g, 15% solution in tetrahydrofuran) is added dropwise over two hours at 20–25° C. to a solution of 4-bromobenzonitrile (10 g) in tetrahydrofuran (80 ml). After addition of water (20 ml), tetrahydrofuran is removed under vacuum. The residue is extracted with toluene (100 ml) and the solvent removed under vacuum. 4-bromo-4'-methoxybenzophenoneimine (3.5 g, 34%) is isolated by column chromatography on Kieselgel 60 using n-hexane/acetone (3:1). $^1$H NMR (CDCl$_3$): 3.84 (s,3H), 6.93(d,2H), 7.41–7.61(m,6H), 9.5(s, 1H).

Comparative Example 2

4-methoxyphenylmagnesium bromide (91 g, 14% solution in tetrahydrofuran) is added over 30 seconds at 20–25° C. to a solution of 4-bromobenzonitrile (10 g), palladium (II) acetate (0.25 g) and triphenylphosphine (0.58 g) in tetrahydrofuran (80 ml). [HPLC: total yield >90%; ratio 4'-methoxybiphenyl-4-carbonitrile to 4-bromo-4'-methoxybenzophenoneimine 1:31].

From these Examples the following conclusions can be drawn:

in an uncatalysed reaction, even with slow addition of the benzonitrile, the competitive benzophenoneimine product is predominantly obtained [see Comparative Example 1]

the palladium-catalysed reaction with slow addition gives a clear predominance of the desired product [see all Examples].

If necessary simple experiments should be carried out to determine which catalyst concentration is most suitable for the particular reactants. For a palladium-based catalyst such as PdCl$_2$/2PPh$_3$ the concentration limit at an addition time of 6–10 hours is about 0.4% molar based on bromobenzonitrile. Above this concentration the displacement of the course of reaction is unequivocally in favour of the desired product. Obviously, deviations from the desired selectivity and yield are possible according to the chosen solvent, reactants and reaction temperature. These problems can however be controlled by choice of a higher catalyst concentration or a longer addition time.

What is claimed is:

1. A method for producing unsymmetrically substituted biphenyls of the general formula

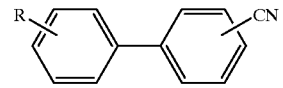

where R=H, alkyl, alkoxy, F, Cl or 4-phenylmethoxy by the palladium-catalysed coupling of an aryl Grignard compound of the general formula

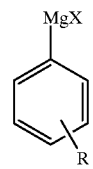

where X=Cl, Br or I; R=H, alkyl, alkoxy, F, Cl or 4-phenylmethoxy and the ring bearing the R substituent is optionally further substituted, with optionally substituted bromobenzonitrile comprising adding the Grignard compound to the bromobenzonitrile slowly at 10–100° C., over a time span of at least 30 minutes, said palladium catalyst being present at a concentration of 0.1 to 20.0% molar based on the benzonitrile.

2. A method as claimed in claim 1, wherein the addition time for the Grignard compound is from 1 to 24 hours.

3. A method as claimed in claim 1, wherein the addition time for the Grignard compound is from 4 to 18 hours.

4. A method as claimed in claim 1, wherein the addition time for the Grignard compound is from 8 to 10 hours.

5. A method as claimed in claim 1, wherein the palladium concentration of the catalyst is 1.0 to 2.0% molar based on the bromobenzonitrile.

6. A method as claimed in claim 1, wherein R is alkyl and has up to 30 carbon atoms.

7. A method as claimed in claim 6, wherein R is alkyl and has up to 20 carbon atoms.

8. A method as claimed in claim 1, wherein R is a straight or branched chain alkyl group or a cycloalkyl group.

9. A method as claimed in claim 1, wherein the aromatic ring of the Grignard compound is further substituted by an acetal or alkyl group.

10. A method as claimed in claim 1, wherein the palladium catalyst is a Pd(0) complex.

11. A method as claimed in claim 10, wherein the Pd(0) complex is $Pd(PPh_3)_4$.

12. A method as claimed in claim 1, wherein the coupling reaction is carried out at a temperature in the range of 20 to 80° C.

13. A method as claimed in claim 1, wherein the bromobenzonitrile is further substituted by an alkyl or alkoxy group, by halogen or by 4-phenylmethoxy.

14. A method as claimed in claim 1, wherein the molar ratio of bromobenzonitrile to Grignard compound is 2:1 to 1:2.

15. A method as claimed in claim 14, wherein the molar ratio of bromobenzonitrile to Grignard compound is between 1:1 and 1:1.2.

* * * * *